United States Patent
Grzeda et al.

(10) Patent No.: US 7,115,421 B2
(45) Date of Patent: Oct. 3, 2006

(54) METHOD AND DEVICE FOR MEASUREMENT OF HEMATOCRIT

(75) Inventors: Barbara R. Grzeda, Schaumburg, IL (US); Jack A. Maggiore, Lombard, IL (US)

(73) Assignee: BioSafe Medical Technologies, Inc., Lake Forest, IL (US)

( * ) Notice: Subject to any disclaimer, the term of this patent is extended or adjusted under 35 U.S.C. 154(b) by 252 days.

(21) Appl. No.: 10/417,697

(22) Filed: Apr. 17, 2003

(65) Prior Publication Data

US 2004/0023399 A1 Feb. 5, 2004

Related U.S. Application Data

(60) Provisional application No. 60/373,303, filed on Apr. 17, 2002.

(51) Int. Cl.
*G01N 33/86* (2006.01)

(52) U.S. Cl. .......................... 436/70; 436/63; 436/165; 436/169; 436/170; 436/177; 436/178; 422/55; 422/56; 422/58; 422/73; 422/101

(58) Field of Classification Search ................. 436/63, 436/70, 164, 165, 169, 170, 177, 178, 175; 422/55, 56, 58, 61, 73, 101; 73/61.65; 600/370
See application file for complete search history.

(56) References Cited

U.S. PATENT DOCUMENTS

| | | | | |
|---|---|---|---|---|
| 4,250,257 A | * | 2/1981 | Lee et al. ....................... | 435/4 |
| 4,340,565 A | * | 7/1982 | Kitajima et al. ............... | 422/56 |
| 5,962,215 A | * | 10/1999 | Douglas et al. ................ | 435/4 |
| 6,197,494 B1 | * | 3/2001 | Oberhardt ....................... | 435/4 |
| 6,406,919 B1 | * | 6/2002 | Tyrrell ........................ | 436/174 |

FOREIGN PATENT DOCUMENTS

| | | | |
|---|---|---|---|
| JP | 8-220088 | * | 8/1996 |
| JP | 8-220089 | * | 8/1996 |
| JP | 2000-146959 | * | 5/2000 |
| WO | 98/00703 | * | 1/1998 |
| WO | 99/57559 | * | 11/1999 |

* cited by examiner

*Primary Examiner*—Maureen M. Wallenhorst
(74) *Attorney, Agent, or Firm*—Olson & Hierl, Ltd.

(57) ABSTRACT

Hematocrit in a blood sample is visualized by separating blood plasma from red blood cells in the blood sample on an absorbent substrate provided with a blood plasma soluble dye. Methods and devices to achieve the visualization are described.

2 Claims, 3 Drawing Sheets

METHOD AND DEVICE FOR MEASUREMENT OF HEMATOCRIT

CROSS-REFERENCE TO RELATED APPLICATION

This application claims priority of U.S. Provisional Application No. 60/373,303, filed on Apr. 17, 2002.

FIELD OF THE INVENTION

This invention relates to a method and apparatus for measuring blood parameters such as hematocrit in a whole blood sample. More particularly the invention relates to a hematocrit measuring device that contains a blood plasma separating membrane and its use.

BACKGROUND OF THE INVENTION

Hemoglobin determination is one of the most frequently performed tests in hospitals. Anemia, or a decrease in hemoglobin concentration, is a sign of an underlying disease process. Mild anemic states often cause no symptoms because of the body's ability to compensate for the deficiency in hemoglobin, at least on a short term basis. With increasing severity of anemia, however, the resulting increased cardiac stress may cause tachycardia, shortness of breath, and headaches. In its most severe form, anemia may lead to coma and death.

A commonly used determinant of hemoglobin concentration in whole blood is hematocrit. Hematocrit is generally defined as the volume fraction of whole blood that is occupied by red blood cells. The hematocrit of a normal healthy person is generally about 45% (about 42 to 52% for men and about 36 to 48% for women). Much lower values than the foregoing are a sign of anemia. Hematocrit can be determined by centrifuging a whole blood sample in a volumetrically calibrated centrifuge tube (or capillary centrifuge tube) to settle all of the red blood cells at the bottom of the tube, leaving the plasma at the top. A "buffy coat" of white blood cells just above the red blood cell layer indicates complete separation. The volume % of red blood cells is then calculated by dividing the volume occupied by the red blood cells by the total volume, and multiplying by 100. Plasma and red blood cells must be disposed of after the test is complete. The test also requires a centrifuge, making it impractical for home use.

The standard laboratory hematocrit test generally requires that the blood be drawn and tested by a clinical technician or other health care provider. Biological waste disposal problems are generated as well. There is an ongoing need, therefore, for a hematocrit testing device that can be utilized by an individual, at home, or by health care professionals, which is relatively simple to use, can be performed with a small, capillary blood sample, that does not require use of a centrifuge, and that minimizes and simplifies blood disposal after the test is complete. The hematocrit measuring device of the present invention fulfills this need.

SUMMARY OF THE INVENTION

A method and device for visualizing hematocrit in a blood sample are provided. The method includes the steps of combining a blood sample with a blood plasma-soluble dye and separating dyed blood plasma from red blood cells present in the blood sample in an absorbent substrate. The dyed blood plasma has a color sufficient to provide a visual impression of the hematocrit level of the blood sample. The visual impression can be quantified by measuring the relative areas of the absorbent substrate occupied by the red blood cells and the dyed plasma, or the linear distances traversed by the red blood cells or dyed plasma through the substrate, and comparing one or more of these measured areas or distances to a calibration curve that correlates the areas or distances to hematocrit levels.

The hematocrit measuring device of the present invention includes a blood plasma separating membrane, capable of separating blood plasma from red blood cells, and optionally, a porous blood application pad, in contact with a blood sample receiving portion of the membrane. At least one of the blood sample receiving portion of the membrane or the blood application pad contains a non-hemolyzing, plasma-soluble dye, having a visible color. Upon application of a pre-determined amount of blood to pad, or directly to the blood sample receiving portion of the membrane, the blood passes into the membrane by capillary (wicking) action, and at least a portion of the dye dissolves in the blood plasma. As the blood wicks through the membrane, the dyed plasma separates from the red blood cells.

The blood plasma separating membrane separates the red blood cells from the dyed plasma, by a process analogous to chromatography, as the sample wicks through the membrane. Red blood cells travel through the membrane slower than the plasma, thus regions of red blood cells and dyed plasma appear in the membrane visually distinct as the red cells are separated from the plasma. The distances traveled by the red blood cells and the plasma after all of the blood has been absorbed by the membrane are directly related to the hematocrit level in a blood sample under consideration.

DESCRIPTION OF PREFERRED EMBODIMENTS

Figures 1, 2:
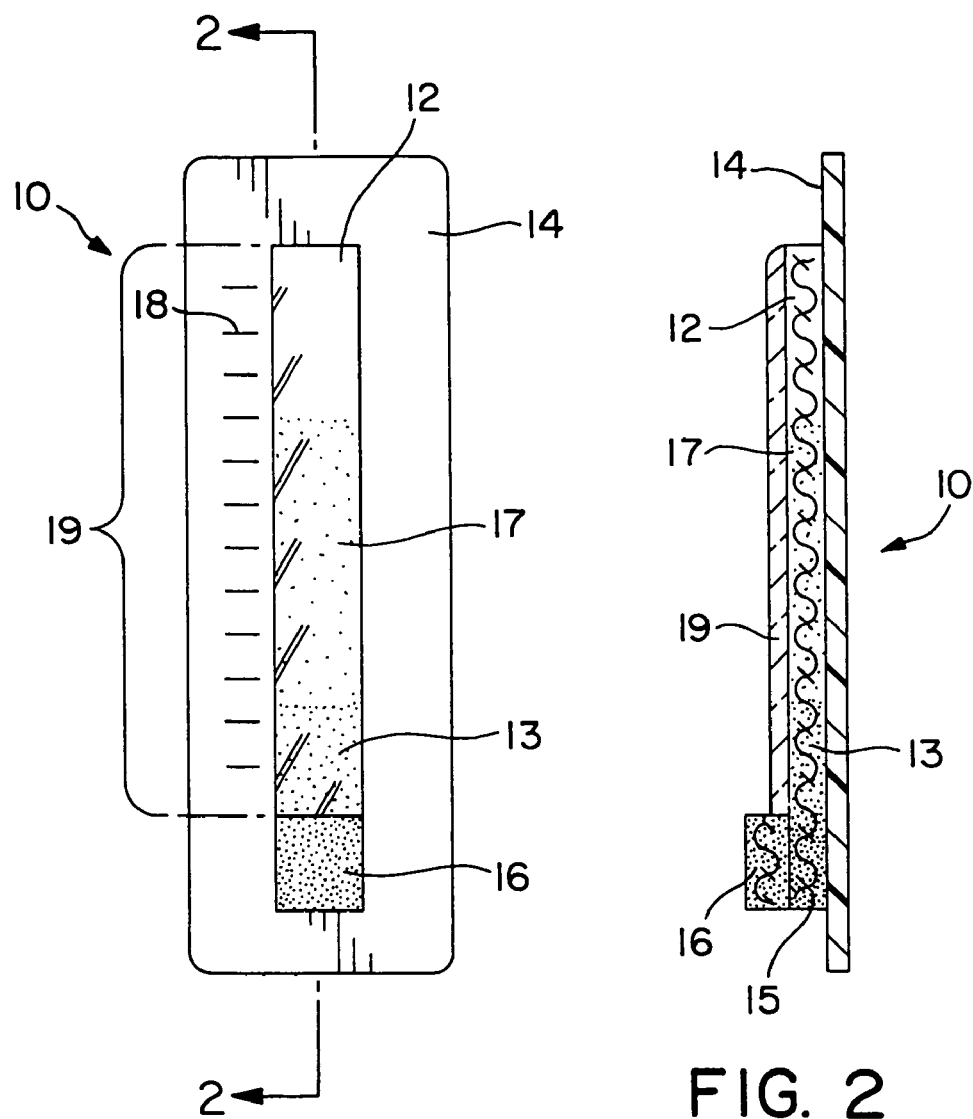
FIG. 1 depicts a preferred embodiment of the hematocrit measuring device of the invention in the form of a hematocrit test card, and including a blood application pad.
FIG. 2 is a cross-sectional side view of the device of FIG. 1 taken along plane 2—2.

A method of visualizing hematocrit in a blood sample is provided, which includes the steps of combining a blood sample with a blood plasma-soluble dye and separating dyed blood plasma from red blood cells present in the blood sample in an elongated absorbent substrate.

A blood sample is drawn into the absorbent substrate by capillary action or like physical processes, and the blood plasma is separated from the blood cells by differential capillary flow within the substrate. The absorbent substrate is selected such that red blood cells and blood plasma are separated in a process similar to chromatography. The separation can be achieved by size exclusion properties of the absorbent substrate or by selective affinity of the absorbent material for blood cells relative to blood plasma. Blood plasma flows more readily through the absorbent substrate than the red blood cells, resulting in a separation of plasma from cells as the blood sample flows through the membrane.

The dyed blood plasma has a color that provides a visual impression of the hematocrit level of the blood sample. The visual impression can be quantified by measuring the relative areas of the absorbent substrate occupied by the red blood cells and the dyed plasma, or the linear distances traversed by the red blood cells or dyed plasma through the substrate, and comparing one or more of these measured areas or distances to a calibration curve relating the areas or distances to hematocrit levels.

A hematocrit measuring device of the present invention comprises an elongated blood plasma separating membrane, capable of separating blood plasma from red blood cells by a process similar to chromatography. In one preferred embodiment, the hematocrit measuring device includes a porous blood application pad, such as a gauze, open cell foam, and the like, which pad is in fluid flow relationship with the membrane and in contact with a blood sample receiving portion of the surface of the membrane. The porous blood application pad contains a plasma-soluble, non-hemolyzing dye. Optionally, the dye can have a contrasting color. Preferably the pad also contains an anticoagulant substance to prevent coagulation of the blood, which can interfere with the hematocrit measurement. When a pre-determined amount of blood (e.g. one drop or about 20 µL) is applied to the pad, the drop is completely absorbed by the pad, and at least a portion of the dye dissolves in the plasma. The blood then is drawn into the membrane by capillary or wicking action. The membrane separates the red blood cells from the plasma as the blood migrates through the membrane.

The pad or membrane can also contain a protein-precipitating agent, such as sulfosalicylic acid, or a tricarboxylic acid, to precipitate plasma proteins and further facilitate the separation of the plasma by the membrane. In addition, the pad or membrane can contain an anticoagulant.

In an alternative preferred embodiment the blood application pad can be omitted, and a blood aliquot can be applied directly to a blood sample receiving portion of the membrane. In this embodiment, the dye and any other chemical additives, such as a protein-precipitating agent or anticoagulant, can be coated directly on the blood sample receiving portion of the membrane or can be absorbed therein.

The membrane preferably contains a surfactant/wetting agent, such as sodium-n-methyl-n-oleoyl taurate (Gerpon T-77; CAS# 137-20-2), t-octylphenoxypolyethoxyethanol (Triton X-100), polyoxyethylene(20) sorbitan monolaurate (Tween 80), 2,4,7,9-tetramethyl-5-decyne-4,7-diolethoxylate(30)(Surfynol 1485), or a poly(oxyethylene-co-oxypropylene) block copolymer (Pluronic F68 or Pluronic L64) in the range of 0.001 to 10% w/v.

The membrane preferably contains a backing material on the surface of the membrane opposite the surface that is in contact with the pad. The backing material can be a sheet or a plate, and is a non-absorbent barrier material that prevents the blood from passing directly through the membrane, thus confining the blood to movement within the membrane.

Typically, such backing material can be a flexible polymeric film or rigid polymeric sheet form substrate such as, for example, a polystyrene sheet, a polyester sheet made from polyethylene terephthalate (PET), a polyolefin sheet made from polyethylene or polypropylene, a polyamide sheet made from polycaprolactam, a modified cellulose film such as cellulose acetate, a polycarbonate sheet, or any other non-absorbent polymeric material. Alternatively the backing substrate can be a glass plate, a metal plate or a metal foil. Any metal that will not interfere with blood plasma separation or react with the blood components or the dye is suitable for use as a backing including, without limitation, aluminum and stainless steel.

One preferred embodiment is shown in FIG. 1 and FIG. 2. FIG. 1 is an external front view of the device and FIG. 2 is a cross-sectional side view. The hematocrit measuring device 10 comprises an elongated strip of blood plasma separating membrane 12 mounted on a card or other rigid or semi-rigid blood impermeable support 14. Porous blood application pad 16 is mounted in contact with a blood sample receiving portion 15 of the surface of membrane 12 at one end of the membrane. Pad 16 contains a plasma-soluble dye absorbed therein. A portion of the support 14 can be printed or engraved with markings 18 indicating distance from the pad or with simple indicators of "normal", "low", or "high" for example, on the same surface of the support as the membrane is mounted to aid in interpreting the result of a hematocrit test performed with the device.

In an alternative embodiment of the hematocrit measuring device of FIG. 1, the volume of blood applied to the membrane can be chosen so that blood having a hematocrit higher than normal will clog the membrane (i.e. exceed the red blood cell absorbing capacity of the membrane) thus preventing the dyed plasma from migrating as far as it would have migrated with blood having a normal hematocrit or a low hematocrit. In such an embodiment, a marking indicator can be printed on the face of the support to indicate the distances traveled by plasma from blood having a normal hematocrit and for blood having abnormally low or high hematocrit. In such embodiment, dyed plasma from low hematocrit blood travels the farthest from the pad 16, whereas dyed plasma from blood having an abnormally high hematocrit travels the shortest distance from the pad. Dyed plasma from normal hematocrit blood travels an intermediate distance from the pad. Thus, if the leading edge of the dyed plasma in the membrane is between pre-determined "low" and "high" hematocrit markings the hematocrit of the blood is deemed to be in "normal" range.

In another alternative embodiment, pad 16 can be omitted and the blood sample receiving portion 15 of membrane 12 can be located in the middle portion of the membrane, in which case, dyed plasma and blood cells metered onto receiving portion 15 migrate toward both ends of the elongated membrane strip.

In the hematocrit measuring device 10 of FIGS. 1 and 2 it is preferred that the visible surface of membrane 12 is protected by a transparent cover sheet 19 (FIG. 2) to protect the membrane from being touched or otherwise contaminated. Sheet 19 can be a transparent polymeric film, a transparent plastic sheet, or a like material.

In use, when a pre-determined amount of blood is applied to pad 16, at least a portion of the dye is dissolved by the blood plasma. As the blood is wicked into the membrane by capillary action, the red blood cells are separated from the dyed plasma 17, with the red blood cells remaining relatively closer to the pad than the more mobile plasma as the blood moves laterally through the membrane. The dye can selected to provide a contrasting color between the red blood cells, the dyed plasma, and the membrane and support, if desired.

The ratio of the distance traveled by the red blood cells 13 to the distance traveled by the dyed plasma is directly related to the hematocrit of the blood. An individual interpreting the result of the test can be provided with separate printed instructions describing how to determine the hematocrit of the blood numerically from the distances traveled by the red blood cells and plasma, as indicated by the markings 18, i.e., whether the hematocrit is "normal", "low", or "high." Alternatively such instructions can be printed on the face or back of the device.

Figure 3:
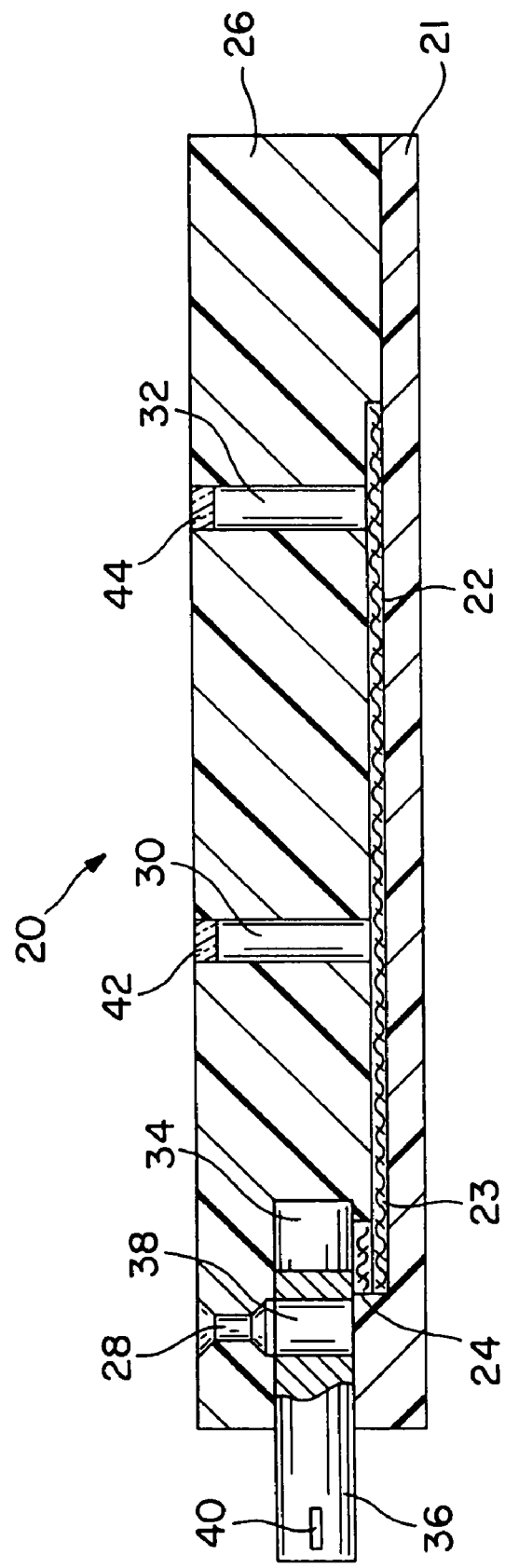
FIG. 3 depicts a particularly preferred embodiment having a housing containing a blood application mechanism.

A particularly preferred embodiment of the hematocrit measuring device of the present invention is shown in a cross-sectional view in FIG. 3. The hematocrit measuring device 20 comprises a lower support housing 21, and a blood plasma separating membrane strip 22 mounted on the lower support housing 21. A porous blood application pad 24 is mounted on a blood sample receiving portion 23 of blood plasma separation membrane 22. Upper housing 26 is mounted over membrane 22 and pad 24, completely enclosing the membrane and pad within the housings 21 and 26. Upper housing 26 defines a fill port 28 and observation ports 30 and 32. The juncture between the lower housing 21 and the upper housing 26, at the end of the device containing pad 24, defines a cavity or lumen 34 adapted to receive a closure lever 36. In the fully open position, depicted in FIG. 3, the closure lever 36 defines a blood receiving chamber 38 that is in fluid connection with fill port 28. When closure lever 36 is pushed into the cavity 34, fill port 28 is blocked by lever 36 and blood receiving chamber 38 is placed in fluid flow relationship with blood application pad 24. A locking mechanism 40 on closure lever 36 secures chamber 38 in the operative fluid flow position after lever 36 is pushed in, and prevents spillage of blood from the device.

Upper housing 26 and lower housing 21 can be secured to one another by one or more fasteners, such as screws, by an adhesive, by a snap-fit mechanism, or any other suitable expedient. The observation ports 30 and 32 in upper housing 26 can be open or can be covered by transparent observation windows 42 and 44, respectively. Windows 42 and 44 can be made of glass or any transparent polymeric resin such as a polycarbonate, a polystyrene, and the like.

In an alternative embodiment of device 20 upper housing 26 can define a single observation window that allows the entire length of membrane 22 to be viewed. Indicator marks can be printed or engraved on the transparent window to allow the relative distances traveled by red blood cells and dyed plasma to be viewed, as was described above for the embodiments of FIGS. 1 and 2.

In using device 20 of FIG. 3 as a test for anemia, a patient lances a finger to draw blood and drops blood from the lanced finger into fill port 28 with closure lever 36 in the open position as illustrated in FIG. 3, so that blood receiving chamber 38 fills with blood. Optionally, an indicator window, not shown, can be included, comprising a port in visual communication with the portion of fill port 28 just above the top of blood receiving chamber 38. When a red color completely fills the indicator window, the patient knows that the required quantity of blood has been deposited in receiving chamber 38. Such indicator windows are well known in the home medical testing kit art.

After the patient has filled chamber 38 with blood, closure lever 36 is pushed into cavity 34 until it is secured by locking mechanism 40. At that point, the blood-filled receiving chamber 38 is in fluid flow relationship with blood application pad 24 or blood sample receiving portion 23 of membrane 22, as the case may be. At least a portion of the dye is dissolved by the blood plasma, as is at least a portion of any other chemical additives also contained within pad 24 or blood sample receiving portion 23 of membrane 22. Blood flows into blood plasma separation membrane 22 and is separated by membrane 22 as described above for the embodiments depicted in FIGS. 1 and 2.

Observation port 30, situated closer to blood sample application portion 23 than port 32, is positioned so that red blood cells from blood having a hematocrit of up to about 65% will be visible through the port. Observation of a red color through port 30 acts as a positive control for the hematocrit test. If red is not visible, it indicates that there was a problem with either the volume of blood being too low or some other problem that invalidates the test. Observation port 32 is situated along the length of membrane 22 such that if the patient's hematocrit is abnormally low (i.e., the patient is anemic) a color of dyed plasma will be visible through port 32, and a red color will be visible through port 30. If the patient's blood has a normal hematocrit, port 32 will have no color visible, whereas a red color will still be observed in port 30. Generally, a red color will be visible in port 30 for any blood sample having a hematocrit in the range of about 20% to about 65%.

Figure 4:
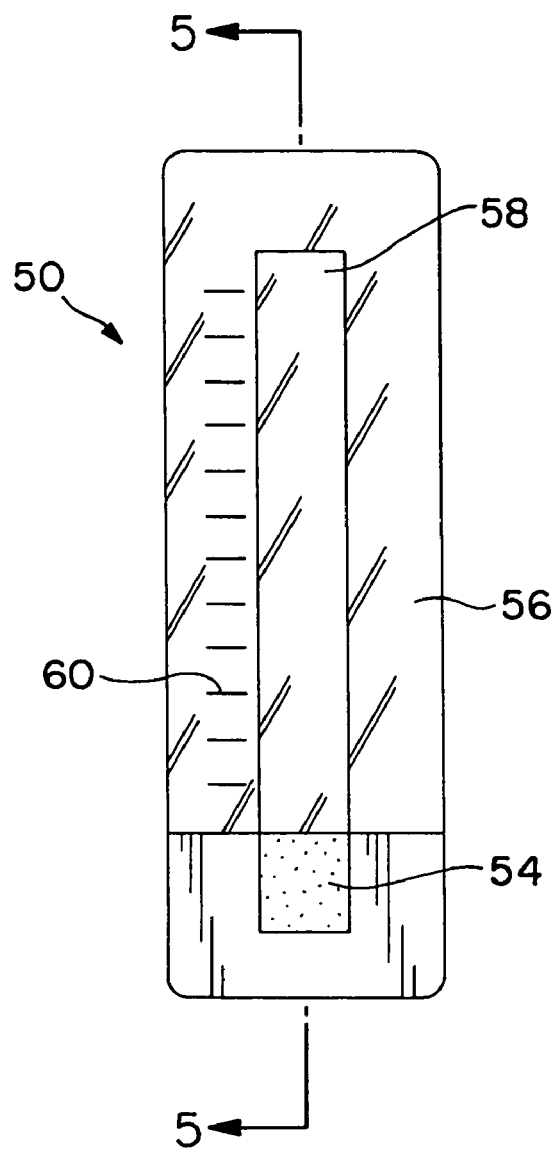
FIG. 4 depicts a preferred embodiment of the hematocrit measuring device of the invention in the form of a hematocrit test card, without a blood application pad.
Figure 5:
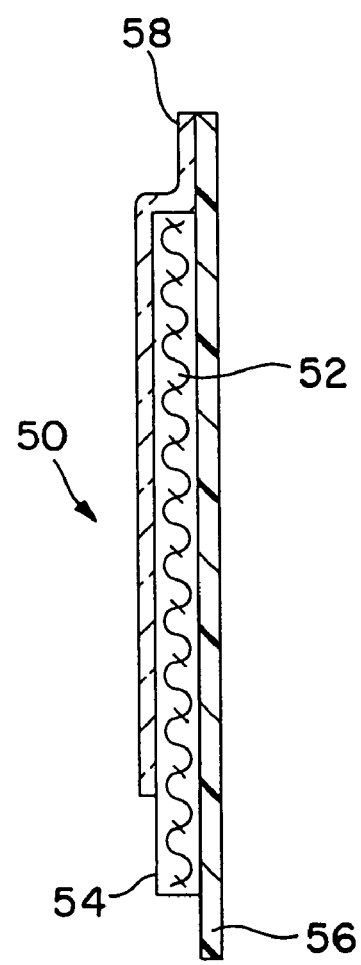
FIG. 5 is a cross-sectional side view of the device of FIG. 4 taken along plane 5—5.

An alternative preferred embodiment of the device of FIG. 1 and FIG. 2, but omitting the blood application pad 16, is shown in FIG. 4 and FIG. 5. In this embodiment, hematocrit measuring device 50 comprises an elongated strip of blood plasma separating membrane 52, having a blood sample receiving portion 54, membrane 52 being mounted on a backing 56. The entire surface of membrane 52, exclusive of blood sample receiving portion 54, and a portion of backing 56, is covered by a transparent film or cover sheet 58. Device 50 also includes markings 60 to aid in determining the distance traversed by the red blood cells and dyed-plasma. A blood sample to be tested for hematocrit is applied directly to blood sample receiving portion 54 of membrane 52.

As in the embodiment shown in FIGS. 4 and 5, the blood application pad 24 of device 20 in FIG. 3 also can be omitted, in which case the blood sample receiving portion 23 of membrane 22 contains the plasma-soluble dye. Alternatively, the dye can be distributed over the entire surface of the membrane, rather than being limited to the blood receiving portion. Generally, a dissolved dye presents a much stronger visual impression than a dye in the dry state. As the plasma moves through he membrane, dye is continuously dissolved in the plasma, thus making the leading edge of the plasma clearly visible and distinguishable from the portions of the membrane that contain only dry dye. Furthermore, the concentration of dye in the leading edge of the plasma generally increases as the plasma migrates through the membrane, leading to a stronger and stronger visual impression as the plasma progresses through the membrane. Coating the whole membrane also simplifies the manufacturing process, since the entire membrane can be dyed without need for precision placement of dye.

The quantity of blood applied to the membrane can affect the apparent hematocrit result. Accordingly, the quantity of blood to be applied is chosen to match the blood holding and separating capacity of the membrane, by methods that are known in the blood plasma separation art. Preferably the blood to be applied is capillary blood obtained by some convenient method such as a "finger stick." A patient lances the tip of a finger using any commercially available finger lance to draw blood. The blood can be applied as a single drop to the pad, or preferably, a capillary tube is applied to the lanced finger to draw a measured quantity of blood, and this capillary tube is then applied to the pad or directly to the blood sample receiving portion of the membrane, thus ensuring that the proper quantity of blood is delivered to the membrane. Optionally, the lumen of the capillary tube can be coated with an anti-coagulant substance to help ensure proper flow of blood from the capillary into the membrane.

In practice, the surface area of the membrane occupied by the red blood cells and dyed plasma, or the distances along the membrane traversed by the red blood cells or the dyed plasma, will depend upon the amount of blood applied to the membrane and upon the specific type of membrane utilized in the device. For a given membrane and blood sample amount, the distances or areas traversed by the dyed plasma and the red blood cells will differ for blood samples having different hematocrit levels. The relationship between the distances or areas and hematocrit level is determined empirically by a simple calibration procedure that can be performed by the device designer. Blood samples having known, but differing hematocrit levels are obtained or prepared by methods well known in the hematological arts. A sufficient quantity of each blood sample is applied to a device as described above, and the distances traversed by the blood cells and the dyed plasma are measured for each sample. The distances are plotted as a function of hematocrit level, or similarly mathematically analyzed, to determine the relationship between distance and hematocrit. This relationship remains constant for a given membrane type and blood sample quantity. Thus, the device can be marked with numerical indicators of hematocrit level, or with high, low and normal markings, for example, such that the user of the device can interpret the clinical results. Alternatively, or in addition, an instruction sheet or brochure can be included with the device to aid in interpreting the results of a blood test performed therewith. An amount of blood that is suitable for the blood separating capacity of the membrane can likewise be determined empirically, by methods known in the blood separation art, or can be obtained from a blood plasma separating membrane supplier.

Materials suitable for use as a blood application pad include gauze-like materials comprising natural fibers, synthetic fibers, glass fibers, and the like; open-celled foamed polymeric resins; porous paper materials; or any other suitable absorbent material that will not materially interfere with the flow of blood from the pad to the blood plasma separating membrane. Preferably the pad comprises polyethylene, glass fiber, or absorbent paper.

Preferred anti-coagulants for use in hematocrit measuring device of the present invention include, without limitation, heparin, ethylenediamine tetraacetic acid (EDTA) and salts thereof, and a citrate salt such as sodium citrate.

Dyes suitable for use in the hematocrit measuring device of the present invention include any plasma-soluble dye that makes the plasma visible and allows convenient viewing of the plasma for the patient using the test. Preferably the dye is non-hemolyzing and has a low affinity for red blood cells. The dye can be any color that permits viewing from the plasma. For example, the dye can be yellow, cyan, blue, green, light shades of magenta, and non-blood-red colored mixtures thereof. Preferably the dye is a green dye or a mixture of cyan (sky blue) and yellow dyes. Preferred dyes include, without limitation, Green S (C.I. FOOD GREEN #4); ALIZARINE CYANINE GREEN F; a blend of FD&C Blue 1 and FD&C Yellow 5; FD&C Green #3 (Fast Green FCF); ALLURA RED (FD&C 40); and Erythrosine (FD&C 3).

Materials suitable as blood separating membranes for use in the present invention include chromatographic filter papers having size exclusion properties, commercial blood plasma separating membranes and the like.

Preferred blood plasma separating membranes include ACCUSEP™ or AES-110 blood plasma separation membrane, manufactured by Schleicher and Schuell (Dassel, Germany). According to the manufacturer, the ACCUSEP™ membrane is a chemically modified microporous membrane, which is a supported nitro-cellulose with open pore structure that allows efficient flow of blood and plasma. The membrane has a higher affinity for red blood cells than plasma, thus, when whole blood is applied to the membrane, plasma flows more readily through the membrane than the red blood cells, affording a separation of plasma from cells.

According to the manufacturer's product literature, the ACCUSEP™ membranes can be laminated to a blood impermeable backing layer. According to the manufacturer, a strip of ACCUSEP™ membrane of about 5 cm length by 0.625 cm width can separate up to about 40 µL of blood.

Filter papers suitable for use as a blood plasma separating membrane filter papers such as AES-110 available from Schleicher and Schuell GmbH, Einbeck, Germany; include, without limitation, Whatman Filter papers such as Whatman F487014, F487-09, and F147-11, available from Whatman Corp., Clifton, N.J.; filter papers such as BTS-SP 300, BTS-SP-200 and BTS-SP-100, available from US Filter Corp., Warrendale, Pa.; Pall HEMASEP® L and HEMASEP® V, available from Pall Corp., Hauppauge, N.Y.; Spectral CO 306Q/99D, S2104g/99B, and X2705G3/99A, available from Spectral Diagnostics, Inc., Toronto, Canada; and like filter papers.

Typically, a suitable blood plasma separating membrane will be porous, having a pore size distribution and mean pore diameter suitable for separation of red blood cells from plasma. Generally, the mean pore diameter of the membrane will be in the range of about 0.1 µm to about 20 µm, more preferably in the range of about 0.2 to about 12 µm, most preferably about 0.4 µm to about 2 µm.

Preferably, in the hematocrit measuring devices of the present invention, the volume of blood applied to the membrane is in the range of about 10 µL to about 60 µL, preferably about 15 µL to about 50 µL. In the device of FIG. 3, the volume of blood receiving chamber 38 is preferably selected to be within this range. Most preferably, the blood receiving chamber 38 has a volume of about 25 µL.

The surface area of the blood sample receiving portion of the membrane preferably is in the range of about 5 to about 40 percent of the total membrane surface area. More preferably, surface area blood sample receiving portion of the membrane is in the range of about 10 to about 30 percent of the total surface area of the membrane, most preferably about 15 to about 25 percent. The blood application pad, when present, is in contact with substantially the entire surface area of the blood sample receiving portion of the membrane.

Preferably, the hematocrit measuring devices of the present invention are individually hermetically sealed in a foil or plastic pouch. The devices are preferably supplied in a kit containing one or more lancets for obtaining blood samples, optional capillary tubes for collection of blood and application of the blood to the device, and instructions for use of the device and interpretation of the test results obtained therewith.

Numerous variations and modifications of the embodiments described above can be effected without departing from the spirit and scope of the novel features of the invention. No limitations with respect to the specific embodiments illustrated herein are intended or should be inferred. The above disclosure is intended to cover by the appended claims all such modifications as fall within the scope of the claims.

We claim:

1. A device suitable for determination of hematocrit in a blood sample, which comprises an elongated blood plasma separating membrane having a blood sample receiving portion containing a blood plasma-soluble dye;

the dye imparting a color to plasma in the blood sample, and the surface area of the blood sample receiving portion of the membrane being in the range of about 5 to about 40 percent of the total surface area of the membrane; wherein the membrane is contained within a housing which defines observation ports for viewing portions of the membrane; wherein the housing further defines a blood filling port and further comprising a closure lever defining a blood receiving chamber, and wherein said blood receiving chamber is brought into fluid flow relationship with the blood sample receiving portion of the membrane by movement of the closure lever into the housing.

2. A device suitable for determination of hematocrit in a blood sample, which comprises an elongated blood plasma separating membrane having a blood sample receiving portion, and a dye-containing porous pad in a liquid flow relationship with the blood sample receiving portion of the membrane, at a contact area therebetween;

the dye imparting a color to the plasma in the blood sample; the surface area of the blood sample receiving portion of the membrane being in the range of about 5 to about 40 percent of the total surface area of the membrane; and the contact area between the porous pad and the blood sample receiving portion of the membrane being substantially equal to the surface area of the blood sample receiving portion of the membrane; wherein the membrane and pad are contained within a housing which defines observation ports for viewing portions of the membrane, wherein the housing further defines a blood filling port and further comprising a closure lever defining a blood receiving chamber, and wherein said blood receiving chamber is brought into fluid flow relationship with the porous pad by movement of the closure lever into the housing.

* * * * *